United States Patent
Hawley et al.

(10) Patent No.: US 9,290,479 B2
(45) Date of Patent: Mar. 22, 2016

(54) SOLID SALT FORMS OF A PYRROLE SUBSTITUTED 2-INDOLINONE

(71) Applicant: Zoetis Services LLC, Florham Park, NJ (US)

(72) Inventors: Michael Hawley, Stonington, CT (US); Changquan Calvin Sun, Hellerup (DK)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 14/620,835

(22) Filed: Feb. 12, 2015

(65) Prior Publication Data

US 2015/0158849 A1 Jun. 11, 2015

Related U.S. Application Data

(60) Division of application No. 13/367,009, filed on Feb. 6, 2012, now Pat. No. 8,987,320, which is a continuation of application No. 12/067,242, filed as application No. PCT/IB2006/002506 on Sep. 8, 2006, now abandoned.

(60) Provisional application No. 60/718,586, filed on Sep. 19, 2005.

(51) Int. Cl.
*C07D 403/06* (2006.01)

(52) U.S. Cl.
CPC .................................. *C07D 403/06* (2013.01)

(58) Field of Classification Search
CPC ..................................................... C07D 403/06
See application file for complete search history.

(56) References Cited

U.S. PATENT DOCUMENTS

| | | | |
|---|---|---|---|
| 6,573,293 B2 | 6/2003 | Tang et al. | |
| 7,053,114 B2 | 5/2006 | Sun et al. | |
| 7,119,209 B2 | 10/2006 | Jin et al. | |
| 7,125,905 B2 | 10/2006 | Tang et al. | |
| 7,211,600 B2 | 5/2007 | Lipson et al. | |
| 7,452,913 B2 * | 11/2008 | Sun et al. | 514/414 |
| 7,572,924 B2 | 8/2009 | Tang et al. | |
| 2006/0009510 A1 | 1/2006 | Havens et al. | |
| 2009/0048327 A1 | 2/2009 | Sun et al. | |

FOREIGN PATENT DOCUMENTS

| | | |
|---|---|---|
| WO | 01/60814 | 8/2001 |
| WO | 03/016305 | 2/2003 |
| WO | 2004/076410 | 9/2004 |
| WO | 2007/034272 | 3/2007 |

OTHER PUBLICATIONS

PharmaceuticallyAcceptableSalt, 2005, www.rsc.org/suppdata/ce/b5/.../b503309h.do.*
PCT International Search Report, PCT/IB2006/002506, mailed Feb. 2, 2007.
Haleblian and McCrone, "Pharmaceutical Applications of Polymorphism", J. Pharm. Sci., 58(8):911-929, 1969.
Liao et al., "Inhibition of constitutively active forms of mutant kit by multitargeted indolinone tyrosine kinase inhibitors", Blood, 100(2) 585-593, 2002.
London et al., "Phase I Dose-Escalating Study SU11654, a Small Molecule Receptor Tyrosine Kinase Inhibitor, in Dogs with Spontaneous Malignancies", Clinical Cancer Research, 9:2755-2768, 2003.
Pryer et al., "Proof of Target for SU11654 Inhibition of KIT Phosphorylation in Canine Mast Cell Tumors" Clinical Cancer Research, 9:5729-5734, 2003.
Zavodovskaya et al., "Evaluation of dysregulation of the receptor tyrosine kinases Kit Flt3 and Met in histiocytic sarcomas of dogs" AJVR 67(4)633-641, 2006.
Newman and Byrn, "Solid-state analysis of the active pharmaceutical ingredient in drug products" DOT 8 (19):898-905, 2003.
Chawla and Bansal "Challenges in Polymorphism of Pharaceuticals", CRIPS, 5(1):9-12, 2004.
London et al., Clinical Cancer Research "Multi-center, Placebo-controlled, Double-blind, Randomized Study of Oral Toceranib Phosphate (SU11654), a receptor Tyrosine Kinase Inhibitor, for the Treatment of Dogs with Recurrent (Either Local or Distant) Mast Cell Tumor Following Surgical Excision" Jun. 1, 2009; vol. 15 pp. 3856-3865.
PCT Written Opinion of the International Searching Authority PCT/IB/2055/002506—mailed with the International Search Report on Feb. 2, 2007.

* cited by examiner

*Primary Examiner* — Sun Jae Yoo
(74) *Attorney, Agent, or Firm* — Gloria K. Szakiel

(57) ABSTRACT

The present invention relates to solid salt forms of the 3-pyrrole substituted 2-indolinone compound 5-[5-fluoro-2-oxo-1,2-dihydro-indol-(3Z)-ylidenemethyl]-2,4-dimethyl-1H-pyrrole-3-carboxylic acid (2-pirrolidin-1-yl-ethyl)-amide. It also relates to polymorphs of the phosphate salt of the amide. The invention further relates to the use of the salts and polymorphs in the treatment of protein kinase related disorders.

4 Claims, 6 Drawing Sheets

SOLID SALT FORMS OF A PYRROLE SUBSTITUTED 2-INDOLINONE

CROSS-REFERENCE TO RELATED APPLICATIONS

This application is a divisional of U.S. application Ser. No. 13/367,009, filed Feb. 6, 2012, which is a continuation of U.S. application Ser. No. 12/067,242, filed Mar. 18, 2008, now abandoned, which was filed under 35 U.S.C. 371 as a US National Stage entry of International Application No. PCT/IB2006/002506, filed Sep. 8, 2006, which claims the benefit of U.S. Provisional Application No. 60/718,586, filed Sep. 19, 2005, now abandoned, the entire contents each of which are incorporated herein by reference.

FIELD OF INVENTION

The present invention relates to solid salt forms of a 3-pyrrole substituted 2-indolinone compound, 5-[5-fluoro-2-oxo-1,2-dihydro-indol-(3Z)-ylidenemethyl]-2,4-dimethyl-1H-pyrrole-3-carboxylic acid (2-pyrrolidin-1-yl-ethyl)-amide. The foregoing compounds modulate the activity of protein kinases ("PKs"). The compounds of this invention are therefore useful in treating disorders related to abnormal PK activity. Pharmaceutical compositions comprising salts of this compound and methods of preparing them are disclosed. The present invention is also directed to polymorphs of the phosphate salt form of the amide.

BACKGROUND

The following is offered as background information only and is not admitted to be prior art to the present invention.

Solids, including pharmaceuticals, often have more than one crystal form, and this is known as polymorphism. Polymorphism occurs when a compound crystallizes in a multiplicity of solid phases that differ in crystal packing. Numerous examples are cited in the standard references of solid state properties of pharmaceuticals, Byrn, S. R., Solid-State Chemistry of Drugs, New Your, Academic Press (1982); Kuhnert-Brandstatter, M., Thermomiscroscopy In The Analysis of Pharmaceuticals, New York, Pergamon Press (1971) and Haleblian, J. K. and McCrone, W. Pharmaceutical applications of polymorphism. *J. Pharm. Sci.*, 58, 911 (1969). Byrn states that, in general, polymorphs exhibit different physical characteristics including solubility and physical and chemical stability.

Because of differences in molecular packing, polymorphs may differ in ways that influence drug release, solid-state stability, and pharmaceutical manufacturing. The relative stability and the interconversions of polymorphs are particularly important to the selection of a marketed drug. A suitable polymorph may hinge upon the issue of physical stability. For example, the selection of a marketed drug may depend upon the availability and selection of a suitable polymorph having desirable characteristics, such as excellent physical stability or the ability to be manufactured in large scale. The performance of the solid dosage form should not be limited by polymorphic transformations during the shelf life of the product. It is important to note that there is no reliable method to predict the observable crystal structures of a given drug or to predict the existence of polymorphs with desirable physical properties.

PKs are enzymes that catalyze the phosphorylation of hydroxy groups on tyrosine, serine, and threonine residues of proteins. The consequences of this seemingly simple activity are staggering since virtually all aspects of cell life (e.g., cell growth, differentiation, and proliferation) in one way or another depend on PK activity. Furthermore, abnormal PK activity has been related to a host of disorders, ranging from relatively non-life threatening diseases such as psoriasis to extremely virulent diseases such as glioblastoma (brain cancer).

Receptor tyrosine kinases (RTKs), a class of PK, are excellent candidates for molecular targeted therapy, because they play key roles in controlling cell proliferation and survival and are frequently dysregulated in a variety of malignancies. The mechanisms of dysregulation include overexpression (Her2/neu in breast cancer, epidermal growth factor receptor in non-small cell lung cancer), activating mutations (KIT in gastrointestinal stromal tumors, fms-related tyrosine kinase 3/Flk2 (FLT3) in acute myelogenous leukemia), and autocrine loops of activation (vascular endothelial growth factor/VEGF receptor (VEGF/VEGFR) in melanoma, platelet-derived growth factor/PDGF receptor (PDGF/PDGFR) in sarcoma).

Aberrantly regulated RTKs have been described in comparable human and canine cancers. For example, aberrant expression of the Met oncogene occurs in both human and canine osteosarcoma. Interestingly, comparable activating mutations in the juxtamembrane (JM) domain of c-kit are seen in 50-90% of human gastrointestinal stromal tumors (GISTs) and in 30-50% of advanced canine MCTs (mast cell tumors). Although the mutations in human GISTs consist of deletions in the JM domain and those in canine MCTs consist of internal tandem duplications (ITDs) in the JM domain, both lead to constitutive phosphorylation of KIT in the absence of ligand binding. The RTKs and their ligands, VEGF, PDGF, and FGF mediate neo-vascularization, known as angiogenesis, in solid tumors. Consequently, by inhibiting the RTKs, the growth of new blood vessels into tumors may be inhibited.

Antiangiogenesis agents, a class of molecules that inhibits the growth of blood vessels into tumors, have much less toxicity to the body compared to conventional anti-cancer drugs. U.S. Pat. No. 6,573,293, incorporated herein by reference, discloses, among other compounds, 5-[5-fluoro-2-oxo-1,2-dihydro-indol-(3Z)-ylidenemethyl]-2,4-dimethyl-1H-pyrrole-3-carboxylic acid (2-pyrrolidin-1-yl-ethyl)-amide (hereinafter "Compound I"). It has the following structure:

Compound I

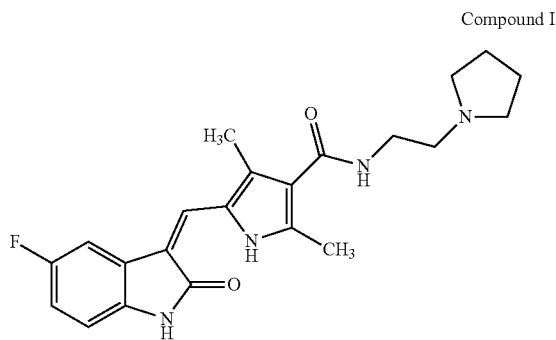 [SMILES: Cc1[nH]c(/C=C2\C(=O)Nc3ccc(F)cc32)c(C)c1C(=O)NCCN1CCCC1]

Compound I is a small molecule that exhibits PK modulating ability. The compound is therefore useful in treating disorders related to abnormal PK activity. It is an inhibitor of the RTKs, PDGFR, VEGFR, KIT, and FLT3. Compound I has been shown to inhibit KIT phosphorylation, arrest cell proliferation, and induce cell cycle arrest and apoptosis in malignant mast cell lines in vitro expressing various forms of mutant KIT. Compound I and related molecules are effective in preclinical models against tumor xenografts arising from cell lines of diverse human tumor origin.

Compound I is useful for treating cancers in companion animals, mainly dogs, and is also useful for the treatment of, inter alia, cancer in humans. Such cancers include, but are not limited to, leukemia, brain cancer, non-small cell lung cancer, squamous cell carcinoma, astrocytoma, Kaposi's sarcoma, glioblastoma, lung cancer, bladder cancer, head and neck cancer, small-cell lung cancer, glioma, colorectal cancer, genitourinary cancer, and gastrointestinal stromal cancer. Also, Compound I is useful for the treatment of diseases related to overexpression of mast cells, including but not limited to, mastocytosis in humans and mast cell tumors in dogs.

Compound I was recently shown to be clinically effective against a number of spontaneous malignancies in dogs. In the study, 11 of 22 canine MCTs showed durable objective responses (partial responses and complete responses) to Compound I treatment; 9 of these MCTs possessed ITDs in the JM domain of c-kit.

Compound I readily crystallizes. Its solubility is about 10 µg/mL in pH 6 phosphate buffer at 25° C. When the compound was synthesized, very fine particles precipitated out of solution during the last step of synthesis. Subsequent isolation of these fine particles by filtration was slow, and a hard cake resulted after filtration. There is a need for a salt of Compound I which has physical stability and desirable physical properties.

SUMMARY OF THE INVENTION

This invention comprises salt forms of Compound I. Five different salt forms of Compound I were synthesized and are described herein. (See Table 1) These include the hydrochloride, fumarate, citrate, phosphate, and ascorbate salts of Compound I. Based on characterization of these salts, the 1:1 phosphate salt, Compound I phosphate, was identified as a salt form with highly desirable characteristics. Polymorph screening revealed the existence of 10 polymorphs of Compound I phosphate, herein named Forms I through X.

In one aspect, this invention provides two salt forms of Compound I, wherein the salt form is selected from the citrate and phosphate salts, and solvates and polymorphs thereof. In one embodiment, the phosphate salt form with a molecular formula of $C_{22}H_{25}FN_4O_2 \cdot H_3O_4P$ is selected. In another embodiment, the phosphate salt form with a melting point from about 285 to about 290° C. is selected. Compound I phosphate has a structure of

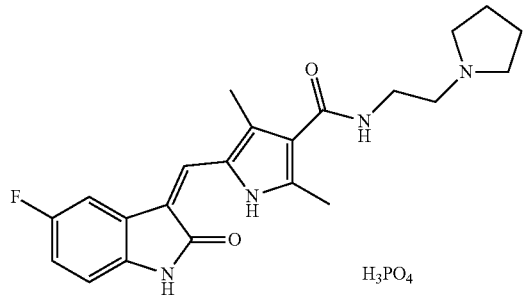

Compound I phosphate

In another embodiment, the citrate salt, Compound I citrate, which has a molecular formula of $C_{22}H_{25}FN_4O_2 \cdot C_6H_8O_7$ is selected. In yet another embodiment, the citrate salt form with a melting point from about 178 to about 183° C. is selected. Compound I citrate has a structure of

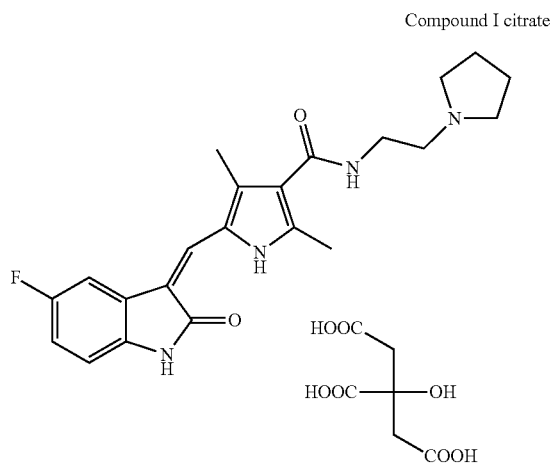 [SMILES: Cc1[nH]c(/C=C2\C(=O)Nc3ccc(F)cc32)c(C)c1C(=O)NCCN1CCCC1 ; O=C(O)CC(O)(CC(=O)O)C(=O)O]

Compound I citrate

A second aspect of the invention is a pharmaceutical composition comprising the phosphate salt or the citrate salt of Compound I, or solvates or polymorphs thereof, and a pharmaceutically acceptable carrier or excipient.

A third aspect of the invention is a method for the modulation of the catalytic activity of protein kinases comprising contacting said protein kinase with the phosphate or citrate salts of Compound I, or solvates or polymorphs thereof. The protein kinase may be selected from the group consisting of receptor tyrosine kinases, non-receptor protein tyrosine kinases, and serine/threonine protein kinases.

A fourth aspect of the invention is a method of preventing or treating a protein kinase related disorder in an organism comprising administering to said organism a therapeutically effective amount of a pharmaceutical composition comprising the phosphate salt or the citrate salt of Compound I, or solvates or polymorphs thereof, and a pharmaceutically acceptable carrier or excipient. In one embodiment, the organism is a human. In another embodiment, the organism is a companion animal. In still another embodiment, the companion animal is a cat or a dog. The protein kinase related disorder may be selected from the group consisting of a receptor tyrosine kinase related disorder, a non-receptor protein tyrosine kinase related disorder, and a serine/threonine protein kinase related disorder. The protein kinase related disorder may be selected from the group consisting of an EGFR related disorder, a PDGFR related disorder, an IGFR related disorder, a c-kit related disorder, and a FLK related disorder. Such disorders include by way of example and not limitation, leukemia, brain cancer, non-small cell lung cancer, squamous cell carcinoma, astrocytoma, Kaposi's sarcoma, glioblastoma, lung cancer, bladder cancer, head cancer, neck cancer, melanoma, ovarian cancer, prostate cancer, breast cancer, small cell lung cancer, glioma, mastocytosis, mast cell tumor, colorectal cancer, genitourinary cancer, gastrointestinal cancer, diabetes, an autoimmune disorder, a hyperproliferation disorder, restenosis, fibrosis, psoriasis, von Heppel-Lindau disease, osteoarthritis, rheumatoid arthritis, angiogenesis, an inflammatory disorder, an immunological disorder, and a cardiovascular disorder.

A fifth aspect of the invention is a method of preparing phosphate salt crystals of base 5-[5-fluoro-2-oxo-1,2-dihydro-indol-(3Z)-ylidenemethyl]-2,4-dimethyl-1H-pyrrole-3-carboxylic acid (2-pyrrolidin-1-yl-ethyl)-amide which comprises introducing a stoichiometric amount of phosphoric acid to the base in a solution comprising a solvent or a mixture of solvents, forcing the phosphate salt in solution to crystallize, separating the phosphate salt crystals from the solvent solution, and drying the crystals. The phosphoric acid may be introduced in an amount which is 40% molar excess to the base. The solvent may comprise isopropanol. The step of separating the crystals from the solvent solution may comprise adding acetonitrile to the solution and rotovapping the solution. The step of separating the crystals from the solvent solution may also comprise filtration.

A sixth aspect of the invention is a method of preparing citrate salt crystals of base 5-[5-fluoro-2-oxo-1,2-dihydro-indol-(3Z)-ylidenemethyl]-2,4-dimethyl-1H-pyrrole-3-carboxylic acid (2-pyrrolidin-1-yl-ethyl)-amide which comprises introducing a stoichiometric amount of citric acid to the base in a solution comprising a solvent or a mixture of solvents, forcing the citrate salt in solution to crystallize, separating the citrate salt crystals from the solvent solution, and drying the crystals. The citric acid may also be introduced in an amount of about 40% molar excess to the base. The solvent may comprise methanol. The step of separating the crystals from the solvent solution may comprise adding acetonitrile to the solution and rotovapping the solution. The step of separating the crystals from the solvent solution may comprise filtration.

In a seventh aspect, the invention provides the polymorphs Forms I-X (as described herein) of the phosphate salt of Compound I. In one embodiment, Form I is provided.

An eighth aspect of the invention is a pharmaceutical composition comprising the Form I polymorph of Compound I phosphate and a pharmaceutically acceptable carrier or excipient.

A ninth aspect of the invention is a method for the modulation of the catalytic activity of protein kinases comprising contacting said protein kinase with the Form I polymorph of Compound I phosphate.

A tenth aspect of the invention is a method of preventing or treating a protein kinase related disorder in an organism comprising administering to said organism a therapeutically effective amount of the Form I polymorph of Compound I phosphate. In one embodiment, the organism is a human or companion animal. In another embodiment, the companion animal is a cat or a dog. Such disorders include by way of example and not limitation, mast cell tumor and mastocytosis.

An eleventh aspect of the invention is a method of preparing polymorphs of Compound I phosphate, which comprises introducing the phosphate salt to a solution comprising a solvent or a mixture of solvents, optionally, adding a bridging solvent to the solution, and separating the polymorph crystals from the solvent solution. The solution may comprise water plus acetonitrile. The solution may comprise methanol. The bridging solvent may be methanol.

A twelfth aspect of the invention is the use of the phosphate or citrate salts of Compound I or the Form I polymorph of the phosphate salt in the preparation of a medicament which is useful in the treatment of a disease mediated by abnormal PK activity.

DETAILED DESCRIPTION OF THE INVENTION

Figure 1:
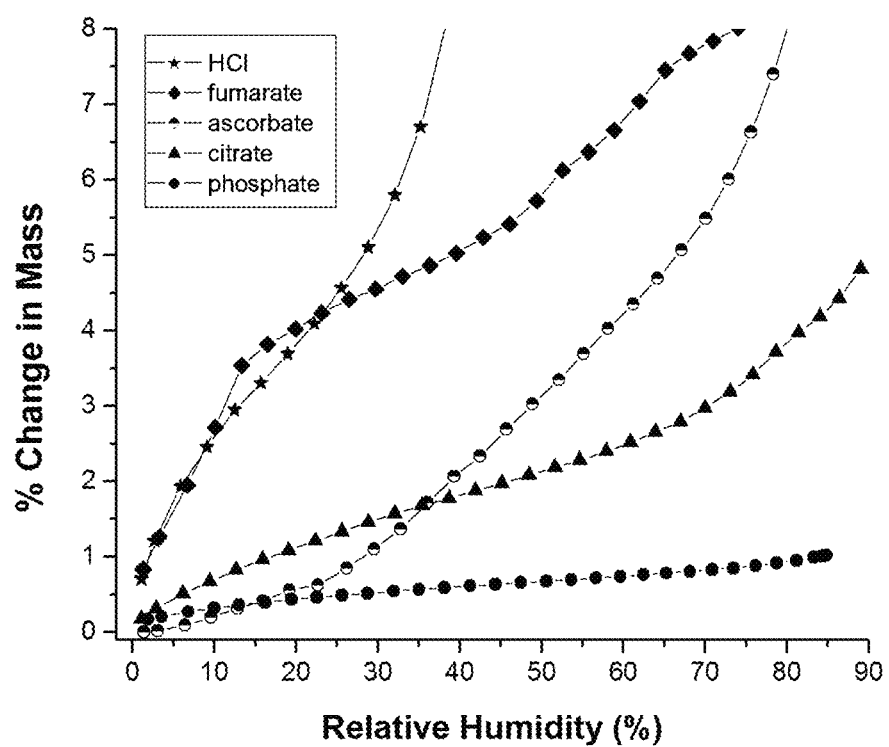
FIG. 1. Moisture sorption data for salts of Compound I.

Definitions. Unless otherwise stated the following terms used in the specification and claims have the meanings discussed below:

The term "C" when used in reference to temperature means centigrade or Celsius.

The term "catalytic activity" refers to the rate of phosphorylation of tyrosine under the influence, direct or indirect, of RTKs and/or CTKs or the phosphorylation of serine and threonine under the influence, direct or indirect, of STKs.

The term "companion animal" refers to domesticated animals offering companionship to humans, and includes, but is not limited to, cats and dogs.

The term "contacting" refers to bringing a compound of the present invention and a target PK together in such a manner that the compound can affect the catalytic activity of the PK, either directly, i.e., by interacting with the kinase itself, or indirectly, i.e., by interacting with another molecule on which the catalytic activity of the kinase is dependent.

The term "$IC_{50}$" means the concentration of a test compound which achieves a half-maximal inhibition of the PK activity.

The term "modulation" or "modulating" refers to the alteration of the catalytic activity of RTKs, CTKs, and STKs. In particular, modulating refers to the activation or inhibition of the catalytic activity of RTKs, CTKs, and STKs, preferably the activation of the catalytic activity of RTKs, CTKs, and STKs, depending on the concentration of the compound or salt to which the RTK, CTK, or STK is exposed or, more preferably, the inhibition of the catalytic activity of RTKs, CTKs, and STKs.

The term "PK" refers to receptor protein tyrosine kinase (RTKs), non-receptor or "cellular" tyrosine kinase (CTKs) and serine-threonine kinases (STKs).

The term "polymorph" refers to a solid phase of a substance, which occurs in several distinct forms due to different arrangements and/or confirmations of the molecules in crystal lattice. Polymorphs typically have different chemical and physical properties.

The term "pharmaceutically acceptable excipient" refers to any substance other than a compound of the invention, added to a pharmaceutical composition.

The term "pharmaceutical composition" refers to a mixture of one or more of the salts of the present invention or the polymorphs of such salts, as described herein, with other chemical components, such as physiologically/pharmaceutically acceptable carriers and excipients. The purpose of a pharmaceutical composition is to facilitate administration of a compound to an organism.

The term "physiologically/pharmaceutically acceptable carrier" refers to a carrier or diluent that does not cause significant irritation to an organism and does not abrogate the biological activity and properties of the administered compound.

The term "polymorph" may also be defined as different unsolvated crystal forms of a compound. The term also includes solvates (i.e., forms containing solvent, or water), amorphous forms (i.e., noncrystalline forms), and desolvated solvates (i.e., forms which can only be made by removing the solvent from a solvate).

The term 'solvate' is used to describe a molecular complex comprising a compound of the invention and one or more pharmaceutically acceptable solvent molecules, for example, ethanol. The term 'hydrate' is employed when said solvent is water.

The term "substantially free" in relation to the amount of a certain polymorph in a sample means that other polymorphs are present in an amount less than about 15 weight percent. In another embodiment, "substantially free" means less than about 10 weight percent. In another embodiment, "substantially free" means less than about 5 weight percent. In still another embodiment, "substantially free" means less than about 1 weight percent. Someone with ordinary skill in the art would understand that the phrase "in an amount less than about 15 weight percent" means that the polymorph of interest is present in an amount of more than about 85 weight percent. Likewise, the phrase "less than about 10 weight percent" means that the polymorph of interest is present in an amount of more than about 90 weight percent, and so on.

The term "therapeutically effective amount" refers to that amount of the compound being administered which will prevent, alleviate, or ameliorate one or more of the symptoms of the disorder being treated, or prolong the survival of the subject being treated. In reference to the treatment of cancer, a therapeutically effective amount refers to that amount which has the effect of:

(1) reducing the size of the tumor;
(2) inhibiting (that is, slowing to some extent, or stopping) tumor metastasis;
(3) inhibiting (that is, slowing to some extent, or stopping) tumor growth, and/or,
(4) relieving to some extent (or eliminating) one or more symptoms associated with the cancer.

Different salt forms of Compound I may be synthesized to obtain a form with better physical properties. The base compound may be in solution. The solution is generally a solvent. In one embodiment, the solution is an alcohol. In another embodiment, the solvent may be isopropanol, methanol, acetonitrile, or water plus acetonitrile. The solution may also comprise a mixture of solvents.

The salts may be crystallized using a stoichiometric addition/crystallization technique. A stoichiometric amount of the counterion is introduced to the base in solution. In one embodiment, the amount of counterion is in a 1:1 ratio to the base. In another embodiment, the amount of counterion is from 0% to about 60% molar excess to the base. In another embodiment, the amount of counterion is from about 10% to about 50% molar excess to the base. In yet another embodiment, the amount of counterion is about 40% molar excess to the base. The counterions may include hydrochloride, fumarate, citrate, phosphate, and ascorbate ions. In one embodiment, the counterion is the phosphate ion. In another embodiment, the counterion is the citrate ion.

The salt in solution is then forced to crystallize by a variety of common techniques including cooling, evaporation, drowning, etc., known to one skilled in the art. Excess solvents may be removed from the samples by methods known to one skilled in the art. In one embodiment, the solvents are removed from the solution by adding acetonitrile (ACN) and rotovapping the solution. The solution may be rotovapped from about 40° C. to about 60° C. In another embodiment, additional solvents may be added to the solution (eg, isopropanol and methyl ethyl ketone) prior to rotovapping. The crystallizations may be conducted in the dark to prevent light-induced isomerization. In one embodiment, the crystals are removed by filtration. In another embodiment, filtration may be performed at ambient laboratory atmosphere.

By these methods, the ascorbate, citrate, fumarate, hydrochloride, and phosphate salts of Compound I were crystallized. Specific examples of crystallization methods are provided below. HPLC analysis may be used to determine purity of the resultant sample. The physical properties of the compounds may be determined by tests known to one skilled in the art, including melting point determination, powder X-ray diffraction, and dynamic moisture sorption gravimetry. Parameters for these tests are described below.

These five salt forms are described herein (See Table 1). These salts of Compound I are often hygroscopic. For example, as can be seen in Table 1, at 80 percent humidity, the hydrochloride salt was about 20 percent water, the fumarate salt was about 9 percent water, and the ascorbate salt was about 6.5 percent water. This characteristic can make use of the salt in a pharmaceutical formulation difficult and can shorten the shelf-life of a formulation. However, two salts, the phosphate and citrate salts, were unexpectedly found to have low moisture uptake, having about 1 percent and about 3.8 percent water at 80 percent relative humidity, respectively.

Based on characterization of these salts, the 1:1 phosphate salt, Compound I phosphate, was identified as a salt form with highly desirable characteristics, including good crystallinity, low moisture uptake, ease of crystallization, good purity, and lack of hydrate. Ten polymorphs of Compound I phosphate, herein named Forms I through X, are also described. The citrate salt also demonstrated desirable characteristics, such as low moisture uptake and good crystallinity.

Polymorphs of the compounds of the present invention are desirable because a particular polymorph of a compound may have better physical and chemical properties than other polymorphic forms of the same compound. For example, one polymorph may have increased solubility in certain solvents. Such added solubility may facilitate formulation or administration of the compounds of the present invention. Different polymorphs may also have different mechanical properties (e.g., different compressibility, compactibility, tabletability), which may influence tableting performance of the drug, and thus influence formulation of the drug. A particular polymorph may also exhibit different dissolution rate in the same solvent, relative to another polymorph. Different polymorphs may also have different physical (solid-state conversion from metastable polymorph to a more stable polymorph) and chemical (reactivity) stability. An embodiment of the present invention contemplates the Form I polymorph of Compound I phosphate, as described herein.

In embodiments of the present invention, pure, single polymorphs as well as mixtures comprising two or more different polymorphs are contemplated. A pure, single polymorph may be substantially free from other polymorphs.

Some embodiments of the present invention contemplate pharmaceutical compositions comprising one or more of the salts of Compound I or the polymorphs of such salts, as described herein, and a pharmaceutically acceptable carrier or excipient.

Polymorphs were generated from concentrated solutions of Compound I phosphate. The concentrated solutions may be in a range of 60 to 100 mg of Compound I phosphate per mL of solution. In one embodiment, about 70 mg of Compound I may be dissolved in 1 mL of phosphoric acid.

The polymorph crystals may be precipitated from a solvent by various methods including, for example, slow evaporation, cooling a supersaturated solution, precipitation from anti-solvents, etc., which are known to one skilled in the art. In one embodiment, the polymorph crystals are generated by adding the solution to an anti-solvent. The anti-solvent may be water plus acetonitrile (ANC), ethanol, methanol, acetone, acetonitrile, THF, ethyl acetate, hexane, methylene chloride ($CH_2Cl_2$), isopropyl alcohol (IPA), methyl ethyl ketone (MEK), and dioxane. In one embodiment, an additional solvent (eg, methanol) may be added. In another embodiment, the samples are allowed to stand overnight prior to removing the crystals. In yet another embodiment, the samples are allowed to stand for three days prior to removing the crystals.

The crystals may be characterized using standard methods known to one skilled in the art, including PXRD dynamic moisture sorption gravimetry, differential scanning calorimetry, thermal gravimetric analysis, and optical microscopy. These techniques are described below.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

The choice of a pharmaceutically acceptable excipient will to a large extent depend on factors such as the particular mode of administration, the effect of the excipient on solubility and stability, and the nature of the dosage form. Examples of excipients include, without limitation, calcium carbonate, calcium phosphate, various sugars and types of starch, cellulose derivatives, gelatin, vegetable oils, and polyethylene glycols.

Carriers and excipients for formulation of pharmaceutically acceptable compositions comprising Compound I are well known in the art and are disclosed, for example, in U.S. Pat. No. 6,573,293, which is incorporated herein in its entirety. Methods of administration for such are also known in the art and also described, for example, in U.S. Pat. No. 6,573,293. Similar methods could also be used to formulate and administer pharmaceutically acceptable compositions of the salts of Compound I, or the polymorphs of such salts, of this invention.

Proper formulation is dependent upon the route of administration chosen. For injection, the compounds of the present invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art. For parenteral administration, e.g., by bolus injection or continuous infusion, formulations may be presented in unit dosage forms, such as in ampoules or in multi-dose containers. The compositions may take such forms as suspensions, solutions, or emulsions in oily or aqueous vehicles, and may contain formulating materials such as suspending, stabilizing, or dispersing agents.

The compounds of the invention may be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques. Parenteral formulations are typically aqueous solutions which may contain excipients such as salts, carbohydrates and buffering agents (preferably adjusted to a pH of from 3 to 9), but, for some applications, they may be more suitably formulated as a sterile non-aqueous solution or as a dried form to be used in conjunction with a suitable vehicle such as sterile, pyrogen-free water. Additionally, suspensions of the compounds of the present invention may be prepared in a lipophilic vehicle. Suitable lipophilic vehicles include fatty oils such as sesame oil, synthetic fatty acid esters, such as ethyl oleate and triglycerides, or materials such as liposomes.

The compounds of the invention may be administered orally. Oral administration may involve swallowing, so that the compound enters the gastrointestinal tract, and/or buccal, lingual, or sublingual administration by which the compound enters the blood stream directly from the mouth. For oral administration, the compounds can be formulated by combining the compounds of the present invention with pharmaceutically acceptable carriers well known in the art. Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999). Other means of topical administration include delivery by electroporation, iontophoresis, phonophoresis, sonophoresis and microneedle or needle-free (e.g. Powderject™, Bioject™, etc.) injection The compounds of the present invention may be formulated for rectal administration, such as suppositories or retention enemas using, for example, conventional suppository bases such as cocoa butter or other glycerides.

The compounds of the present invention may also exist in unsolvated and solvated forms.

The embodiments of the present invention also contemplate a method for the modulation of the catalytic activity of a PK comprising contacting said PK with a one or more of the salts of Compound I or the polymorphs of such salts of the present invention. Such "contacting" can be accomplished "in vitro," i.e., in a test tube, a petri dish, or the like. In a test tube, contacting may involve only a compound and a PK of interest or it may involve whole cells. Cells may also be maintained or grown in cell culture dishes and contacted with a compound in that environment. In this context, the ability of a particular compound to affect a PK-related disorder, i.e., the $IC_{50}$ of the compound, defined below, can be determined before use of the compounds is attempted in vivo with more complex living organisms. For cells outside the organism, multiple methods exist, and are well-known to those skilled in the art, to get the PKs in contact with the compounds including, but not limited to, direct cell microinjection and numerous transmembrane carrier techniques.

Embodiments of the present invention contemplate a method for treating or preventing a protein kinase related disorder in an organism (e.g., a companion animal or a human) comprising administering a therapeutically effective amount of a pharmaceutical composition comprising one or more of the salts of Compound I or the polymorphs of such salts of the present invention and a pharmaceutically acceptable carrier or excipient to the organism.

In an embodiment of the present invention, the protein kinase related disorder is selected from the group consisting of a receptor tyrosine kinase related disorder, a non-receptor tyrosine kinase related disorder, and a serine-threonine kinase related disorder. In another embodiment of the present invention, the protein kinase related disorder is selected from the group consisting of an EGFR related disorder, a PDGFR related disorder, an IGFR related disorder, and a FLK related disorder.

The receptor protein kinase whose catalytic activity is modulated by a compound of this invention is selected from the group consisting of EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R and FGFR-4R. The cellular tyrosine kinase whose catalytic activity is modulated by a compound of this invention is selected from the group consisting of Src, Frk, Btk, Csk, Abl, ZAP70, Fes/Fps, Fak, Jak, Ack, Yes, Fyn, Lyn, Lck, Blk, Hck, Fgr and Yrk. The serine-threonine protein kinase whose catalytic activity is modulated by a compound of this invention is selected from the group consisting of CDK2 and Raf.

In yet another embodiment of the present invention, the protein kinase related disorder is selected from the group consisting of squamous cell carcinoma, astrocytoma, Kaposi's sarcoma, glioblastoma, lung cancer, bladder cancer, head and neck cancer, melanoma, ovarian cancer, prostate cancer, breast cancer, small cell lung cancer, glioma, colorectal cancer, genitourinary cancer, gastrointestinal cancer, mastocytosis, and mast cell tumors. In an embodiment of the present invention, the protein kinase related disorder is selected from the group consisting of diabetes, an autoimmune disorder, a hyperproliferation disorder, restenosis, fibrosis, psoriasis, von Heppel-Lindau disease, osteoarthritis, rheumatoid arthritis, angiogenesis, an inflammatory disorder, an immunological disorder, and a cardiovascular disorder.

Pharmaceutical compositions suitable for use in the present invention include compositions wherein the active ingredients are contained in an amount sufficient to achieve the intended purpose, e.g., the modulation of PK activity or the treatment or prevention of a PK-related disorder.

Determination of a therapeutically effective amount is well within the capability of those skilled in the art, especially in light of the detailed disclosure provided herein. For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture. Such information can then be used to more accurately determine useful doses in humans or companion animals.

In practice, the amount of the compound to be administered ranges from about 0.001 to about 100 mg per kg of body weight, such total dose being given at one time or in divided doses. The amount of a composition administered will, of course, be dependent on the subject being treated, the severity of the affliction, the manner of administration, the judgment of the prescribing physician or veterinarian, etc. In cases of local administration or selective uptake, the effective local concentration of the drug may not be related to plasma concentration and other procedures known in the art may be employed to determine the correct dosage amount and interval.

Embodiments of the present invention also contemplate a method of treating cancer in companion animals comprising administering a pharmaceutical composition comprising one or more of the salts of Compound I or the polymorphs of such salts of the present invention and a pharmaceutically acceptable carrier or excipient.

Additionally, it is contemplated that the salts of Compound I or the polymorphs of such salts, as described herein, would be metabolized by enzymes in the body of an organism such as a companion animal or a human being to generate a metabolite that can modulate the activity of the protein kinases. Such metabolites are within the scope of the present invention.

Compounds of the invention may be administered alone or in combination with one or more other compounds of the invention or in combination with one or more other drugs (or as any combination thereof). It is also contemplated that the salts of Compound I or the polymorphs of such salts, as described herein, might be combined with other chemotherapeutic agents for treatment of the diseases and disorders discussed above. For example, a compound of the present invention may be combined with fluorouracil alone or in further combination with leukovorin or other alkylating agents. A compound of the present invention may be used in combination with other antimetabolite chemotherapeutic agents such as, without limitation, folic acid analogs or the purine analogs. A compound may also be used in combination with natural product based chemotherapeutic agents, antibiotic chemotherapeutic agents, enzymatic chemotherapeutic agents, platinum coordination complexes, and hormone and hormone antagonist. It is also contemplated that a compound of the present invention could be used in combination with mitoxantrone or paclitaxel for the treatment of solid tumor cancers or leukemias.

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLES

Example 1

Synthesis of Compound I, ie. 5-(5-Fluoro-2-oxo-1,2-dihydro-indol-3-ylidenemethyl)-2,4-dimethyl-1H-pyrrole-3-carboxylic acid (2-pyrrolidin-1-yl-ethyl)-amide As described in U.S. Pat. No. 6,574,293 (example 129) 5-Fluoro-1,3-dihydro-indol-2-one was condensed with 5-formyl-2,4-dimethyl-1H-pyrrole-3-carboxylic acid (2-pyrrolidin-1-yl-ethyl)-amide to give Compound I.

Scale-Up Procedure. 5-Formyl-2,4-dimethyl-1H-pyrrole-3-carboxylic acid (61 g), 5-fluoro-1,3-dihydro-indol-2-one (79 g), ethanol (300 mL) and pyrrolidine (32 mL) were refluxed for 4.5 hours. Acetic acid (24 mL) was added to the mixture and refluxing was continued for 30 minutes. The mixture was cooled to room temperature and the solids collected by vacuum filtration and washed twice with ethanol. The solids were stirred for 130 minutes in 40% acetone in water (400 mL) containing 12 N hydrochloric acid (6.5 mL). The solids were collected by vacuum filtration and washed twice with 40% acetone in water. The solids were dried under vacuum to give 5-[5-fluoro-2-oxo-1,2-dihydro-indol-(3Z)-ylidenemethyl]-2,4-dimethyl-1H-pyrrole-3-carboxylic acid (86 g, 79% yield) as an orange solid.

5-[5-Fluoro-2-oxo-1,2-dihydro-indol-(3Z)-ylidenemethyl]-2,4-dimethyl-1H-pyrrole-3-carboxylic acid (100 g) and dimethylformamide (500 mL) were stirred and benzotriazol-1-yloxytris(dimethylamino)phosphonium hexafluorophosphate (221 g), 1-(2-aminoethyl)pyrrolidine (45.6 g) and triethylamine (93 mL) were added. The mixture was stirred for 2 hours at ambient temperature. The solid product was collected by vacuum filtration and washed with ethanol. The solids were slurry-washed by stirring in ethanol (500 mL) for one hour at 64° C. and cooled to room temperature. The solids were collected by vacuum filtration, washed with ethanol, and dried under vacuum to give 5-[5-fluoro-2-oxo-1,2-dihydro-indol-(3Z)-ylidenemethyl]-2,4-dimethyl-1H-pyrrole-3-carboxylic acid (2-pyrrolidin-1-yl-ethyl)-amide (101.5 g, 77% yield).

Example 2

Synthesis of Salts of Compound I

Example 2A

Compound I Phosphate 2.67 mMoles of Compound I was added to a flask with 40 mL 0.092 M phosphoric acid (about a 40% molar excess assuming a 1:1 salt) and 40 mL isopropanol. Then, acetonitrile was continuously added to the aqueous solution in 30 mL aliquots, as the solution was rotovapped at 60° C. to remove the water. In all, 120 mL of acetonitrile was used to remove the water from the solution. The crystals were filtered and air-dried. Crystals were free flowing and orange; 1.09 grams were collected for an 83% yield.

Example 2B

Compound I Citrate 2.64 mMoles of Compound I was added to a flask with 34 mL 0.1M citric acid (3.4 mMoles) and 35 mL methanol. This solution was rotovapped at 50° C. Reducing the volume of this solution produced crystals of poor crystallinity, so 20 mL isopropanol and 10 mL of methyl ethyl ketone were added to dissolve the solid. This mixture was rotovapped at 60° C. and produced orange crystals. The crystals were filtered and air-dried. The yield for this process was about 60%, and could have been improved by reducing the solvent volume further before filtration.

Example 3

Physical Properties of Salts of Compound I

Methods. Tests to determine the physical properties of the salts of Compound I included melting point determination, HPLC purity, powder X-ray diffraction, and dynamic moisture sorption gravimetry.

Powder X-ray Diffraction (PXRD). Powder XRD was performed using a Scintag X2 Advanced Diffraction System (lab 259-1088, controlled by Scintag DMS/NT 1.30a and Microsoft Windows NT 4.0 software. The system uses a Copper X-ray source (45 kV and 40 mA) to provide $CuK\alpha_1$ emission of 1.5406 Å and a solid-state Peltier cooled detector. The beam aperture was controlled using tube divergence and anti-scatter slits of 2 and 4 mm and detector anti-scatter and receiving slits of 0.5 and 0.2 mm width. Data were collected from 2 to 35° two-theta using a step scan of 0.03°/step with a counting time of one second per step. Scintag round, top loading stainless steel sample holders with 9 mm diameter inserts were utilized for the experiments. Powders were packed into the holder and were gently pressed by a glass slide to ensure coplanarity between the sample surface and the surface of holder.

Dynamic Moisture Sorption Gravimetry (DMSG). DMSG isotherm was collected on a temperature controlled atmospheric microbalance. Approximately 10 mg samples were placed in the sample pan of the balance. The humidity was sequentially varied from room relative humidity (RH) to 0% RH and was then increased to 90% RH followed by a decrease of RH to 0% again in 3% RH steps. The mass was then measured every two minutes. The RH was stepped to the next target value when change of the sample mass was less than 0.5 µg in 10 min. The Visual Basic program dmsgscn2.exe was used to control the data collection and export the information to an Excel spreadsheet.

Results. Table 1 shows a summary of data for the ascorbate, citrate, fumarate, hydrochloride, and phosphate salts of Compound I. HPLC analysis suggested that the salts were of relatively high purity, and no significant change in the purity was induced through the salt formation process.

TABLE 1

Summary of salts synthesized for Compound I

| Counterion | Salt Crystallized | Melting point (° C.) | % water at 80% RH | HPLC purity* | % Isomer* |
|---|---|---|---|---|---|
| none (free base) | NA | 257 | ~1% | 97.8 | 0.63 |
| hydrochloride | Yes | 96 | ~20% | 97.7 | 2.29 |
| fumarate | Yes | NA | ~9% | 97.3 | 1.96 |
| citrate | Yes | 181 | ~3.8% | 98.2 | 1.38 |
| phosphate | Yes | 288 | ~1% | | |
| ascorbate | Yes | 245 | ~6.5% | | |

*area percent under the peaks in the HPLC

The hydrochloride, fumarate, and ascorbate salts were very hygroscopic (see FIG. 1). The other two salts (citrate and phosphate) had lower moisture sorption profiles, absorbing less than 3% water at 70% relative humidity.

Figure 2:
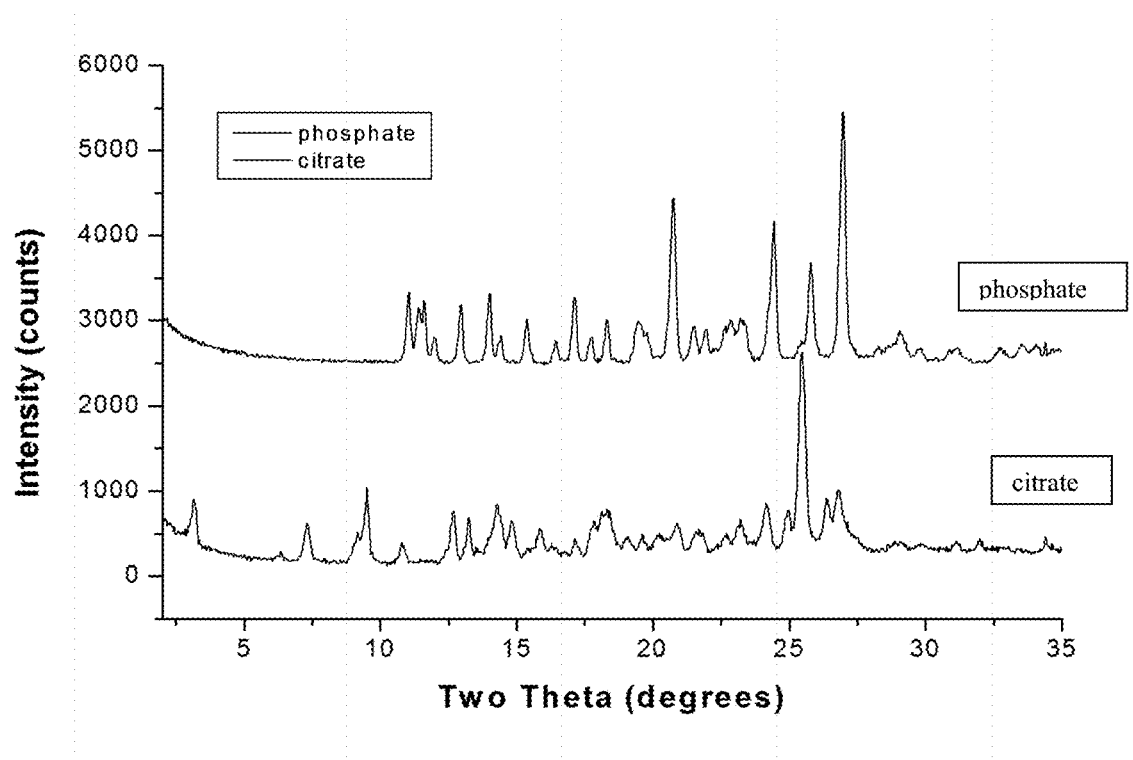
FIG. 2. Powder X-ray Diffraction patterns for Compound I citrate and Compound I phosphate.

The powder X-ray patterns indicated that the phosphate and citrate salts were of relatively high crystallinity. (see Tables 2 and 3; and FIG. 2).

TABLE 2

PXRD Peaks of Compound I Phosphate

| Two-Theta Angle* (degree) | Relative Intensity** (arbitrary) |
|---|---|
| 11.1 | 23.5 |
| 11.5 | 24.0 |
| 11.6 | 19.9 |
| 12.0 | 8.9 |
| 13.0 | 22.0 |
| 14.0 | 25.9 |
| 14.5 | 7.0 |
| 15.4 | 15.0 |
| 16.5 | 7.5 |
| 17.2 | 27.7 |
| 17.8 | 9.5 |
| 18.3 | 16.6 |
| 19.4 | 11.6 |
| 19.6 | 11.2 |
| 19.8 | 9.8 |
| 20.8 | 58.2 |
| 21.6 | 11.8 |
| 22.0 | 9.5 |
| 22.7 | 9.2 |
| 22.9 | 12.4 |
| 23.2 | 12.8 |
| 23.4 | 10.3 |
| 24.4 | 48.8 |
| 25.8 | 30.4 |
| 27.0 | 100.0 |
| 29.2 | 7.4 |
| 29.2 | 7.4 |
| 33.5 | 5.1 |

*±0.1°
**The relative intensity for each peak is determined by normalizing its intensity to that of the strongest peak at 27.0° angle as 100

TABLE 3

PXRD Peaks of Compound I Citrate

| Two-Theta Angle* (degree) | Relative Intensity** (arbitrary) |
|---|---|
| 3.2 | 20.4 |
| 7.3 | 17.7 |
| 9.2 | 14.4 |
| 9.5 | 39.1 |
| 10.8 | 9.5 |
| 12.7 | 23.5 |
| 13.2 | 19.6 |
| 14.3 | 23.5 |
| 14.8 | 16.7 |
| 15.9 | 11.3 |
| 17.2 | 8.3 |
| 17.8 | 11.9 |
| 18.2 | 19.8 |
| 18.3 | 19.5 |
| 19.6 | 6.8 |
| 20.9 | 11.1 |
| 21.6 | 8.9 |
| 21.7 | 10.5 |
| 21.8 | 8.9 |
| 23.2 | 13.2 |
| 24.2 | 20.3 |
| 24.9 | 15.9 |
| 25.5 | 100.0 |
| 26.4 | 20.9 |
| 26.8 | 26.5 |
| 27.1 | 10.8 |
| 32.0 | 6.3 |
| 34.4 | 8.1 |

*±0.1°
**The relative intensity for each peak is determined by normalizing its intensity to that of the strongest peak at 25.5° angle as 100

Example 4

Preparation and Characterization of Compound I Phosphate

Example 4A

Preparation of Compound I Phosphate

Compound I free base was used to prepare the phosphate salt. A sample (lot number 35282-CS-51) of Compound I phosphate was prepared as described above. 4 mL of 0.977 M phosphoric acid was added to 1.095 g of free base in a flask immediately followed by adding 4 mL of acetonitrile. A suspension was obtained. The suspension was heated slightly on a hot-plate. Adding 40 mL of water and heating while stirring for about one hour did not completely dissolve the solid. The solid was filtered and washed with 10 mL of acetonitrile. PXRD showed it was the phosphate salt of Compound I.)

Example 4B

Characterization of Compound I Phosphate

Lot 35282-CS-51 was named polymorph Form I of Compound I Phosphate. It has high crystallinity, good flowability, and large crystal size. Both the absence of the melting event at the melting temperature of Compound I free base (free base polymorph Form A, 256° C.; free base polymorph Form B, 259° C.) and the presence of high melting points (281-297° C.) of the solids suggested that the crystals of Lot 35282-CS-51 are a different salt form and not Compound I free base. The purity of the lot was 99.6% by HPLC.

Example 4C

Estimation of Solubility of Compound I Phosphate

Samples of 1-2 mg of Compound I phosphate (lot 35282-CS-51) were transferred to 10 mL glass vials (tared) and were weighed (accurate to 0.1 mg). Solvents were added to the vials (one solvent to each vial) in a step-wise fashion, with 0.5 mL of solvent added at each step. Solvents used were buffer (pH=2), buffer (pH=5), water, methanol, tetrahydrofuran (THF), acetonitrile, and acetone. After each addition, the vial was capped and shaken. The dissolution of solid was visually observed. If no obvious dissolution was observed, more solvent was added immediately. If dissolution was apparent, the vial was left on the bench for at least 30 minutes before the next addition of solvent. This step was repeated until no crystals were visible against a black and a white background. The solubility was then bracketed by dividing the weight of the compound by the final volume and the volume before the last addition. If a solid remained after the addition of 10 mL of solvent, the solubility was expressed as less than the weight divided by the final volume. If the solid was completely dissolved after the first addition of solvent, the solubility was expressed as greater than the weight divided by the solvent volume. All experiments were conducted at room temperature.

The estimated solubilities of Compound I phosphate in various solvents are presented in Table 4 along with solubilities of the free base, expressed as mg/mL. The solubility of Compound I phosphate is lower than that of Compound I free base in the same solvent, except in water (at various pH levels). The solubility of Compound I phosphate depends on the pH value of a solution, and becomes considerably higher (>3 mg/mL) at pH 2 or lower. The melting point of Compound I phosphate (lot 35282-CS-51) is about 281-297° C., which is substantially higher than the melting point of Compound I free base (free base polymorph Form A, 256° C.; free base polymorph Form B, 260° C.). One important result is that the wettability of Compound I phosphate with water is much better than that of Compound I free base.

TABLE 4

Estimated solubility of Compound I free base and Compound I phosphate in various solvents at 23° C.

| | Solvent | Solubility of Compound I free base (polymorph Form A) (mg/mL) | Solubility of Compound I phosphate (mg/mL)$^d$ |
|---|---|---|---|
| 1 | buffer (pH = 2)$^a$ | 3.11 | 5.9-7.4 |
| 2 | buffer (pH = 5)$^b$ | 0.005 | |
| 3 | water | NA$^c$ | ~0.29$^e$ (some particles stuck on the vial wall and did not dissolve) |
| 4 | methanol | 0.21-0.31 | ~0.14 |
| 5 | THF | 0.32-0.4 | <<<0.19 |
| 6 | Acetonitrile | <<0.08 | <<<0.13 |
| 7 | Acetone | <<0.16 | <<<0.2 |

$^a$pH = 2 buffer is made of HCl and KCl
$^b$pH = 5 buffer is made of potassium acid phthalate and sodium hydroxide.
$^c$Not available but expected <0.005 mg/mL.
$^d$1 g of Compound I phosphate is equivalent to 0.802 g of Compound I free base.
$^e$The final solution pH value is 4.91.

Example 5

Generation of Compound I Phosphate Polymorphs

The low solubilities of Compound I phosphate seen in Example 4C indicated that solutions of highly concentrated (60-100 mg/mL, dark orange-red) Compound I phosphate would be beneficial to precipitate polymorphs of Compound I phosphate from various solvents. Such concentrated solutions were prepared by dissolving Compound I free base in about 1 M phosphoric acid. For example, about 70 mg of Compound I free base could be dissolved in 1 mL of 1M phosphoric acid. However, the amount of Compound I free base and phosphoric acid used depended on the desired concentration and batch size of the solution. In the example in which the precipitate was vacuum filtered immediately after precipitation, about 1 mL of the desired solution was then dripped into about 10 mL of ten anti-solvents to precipitate the salt crystals out. These solvents were water plus acetonitrile (ANC), ethanol, methanol, acetone, acetonitrile, THF, ethyl acetate, hexane, methylene chloride (CH$_2$Cl$_2$), and isopropyl alcohol (IPA). In the example in which the precipitate was vacuum filtered after standing overnight or for three days, the additional solvents of methyl ethyl ketone (MEK) and dioxane were used. Some organic solvents, e.g., ethyl acetate, hexane, CH$_2$Cl$_2$, are not miscible with water and two layers of solvents were observed. Only a little precipitation was seen at the interface even minutes after addition. In those cases, about 1 mL of methanol was added as a bridging solvent, to increase the miscibility between the two layers. Methanol appeared to work well to increase the miscibility because colorless organic layer became yellow as soon as methanol was added. The vial was then shaken vigorously by hand for about one minute. The solids precipitated from organic solvents were vacuum filtered both immediately after precipitation (within 20 min) and after standing overnight or for three days in order to isolate both metastable and stable polymorphs. The powder was then analyzed. The different solids were numbered in the order of discovery.

Example 6

Characterization of the Polymorphs of Compound I Phosphate

Example 6A

Characterization Methods

All powders obtained from the above polymorph screening procedures were analyzed by PXRD, as described in Example 3 above. When a new PXRD pattern was observed, complementary techniques were also used to characterize the solids, including dynamic moisture sorption gravimetry (also described in Example 3), differential scanning calorimetry, thermal gravimetric analysis (when necessary), and optical microscopy.

Differential Scanning calorimetry (DSC). DSC data were obtained using a DSC calorimeter (TA Instruments 2920). Powder (1-5 mg) was packed in an aluminum DSC pan. An aluminum lid was place on top of the pan and was crimped. The crimped pan was placed in the sample cell along with an empty pan as a reference. Temperatures were increased to 300 or 350° C. from 30° C. at a rate of 10° C./min unless otherwise specified.

Thermogravimetry (TGA). TGA experiments were performed using a high resolution analyzer (TA Instruments model 2950). The TA Instruments Thermal Solutions™ for NT (version 1.3L) was used for data collection, and the Universal Analysis™ for NT (version 2.4F) was used for data analysis. Samples (5-10 mg) were placed onto a aluminum pan which was further placed on a platinum weighing pan before being heated. The weights of the aluminum and platinum pans were tared prior to loading the samples. The temperature was increased from 30° C. to 300° C. linearly at a rate of 10° C./min. Dry nitrogen purge was used.

Polarized Light Microscopy. Microscopy was conducted on an Olympus BHSP polarized light microscope. Powder was suspended in silicone oil and dispersed between a microscopy slide and a cover slip. Prior to observation, the cover slip was gently rubbed against the slide to render good dispersion of the particles.

Example 6B

Characterization Immediately After Precipitation

The results are summarized in Table 5. Precipitation took place as soon as the acidic solution was mixed with the anti-solvents. At first, the precipitates were loose flocs. The colors were yellow or light-orange in general. The resulting solid was sticky. The microscopic observation of these solids indicated that they were constituted of very small crystallites with good birefringence under polarized light. At least six different PXRD patterns were observed on solids obtained from nine solvent systems. (See FIG. 3) The amide side-chain on this molecule is flexible and it undertakes different conformations in free base Form B and in its hydrochloride salt. Therefore, the molecule in the different solid forms may be conformational polymorphs. The PXRD patterns of solids precipitated from ethyl acetate, hexane, and IPA appeared the same. However, a detailed comparison with other PXRD patterns was difficult because of the low diffraction signals of solids from these three solvents. Consequently, they were not assigned as a new form. The precipitate from methanol is the same as the reference lot 35282-CS-51 (assigned as Form I). TGA data of all precipitates indicated residue solvent at a level of 1.7-4.7%. Of these solids, the one from $CH_2Cl_2$ appeared to be a solid with retained solvent in crystals. The TGA curve showed an abrupt decrease in sample weight at a temperature about 125° C. (see FIG. 4). This event is recorded as an endotherm at about the same temperature by DSC. In addition, this powder was constituted of crystals of well-defined morphology and was free-flowing, a very different property from other lots of precipitates. The powder exhibited medium crystallinity by PXRD but good crystallinity when observed by polarized-light microscope. Other lots were constituted of very fine crystallites. On DSC curve of these powders, a broad and shallow endotherm was seen as soon as the sample was loaded to the sample cell. This observation is reflected by TGA as a gradual weight loss from the beginning of heating on TGA. Therefore, for these lots, the residual solvents were probably surface adsorbed solvents and were not solvents in the crystal lattice.

Figure 3:
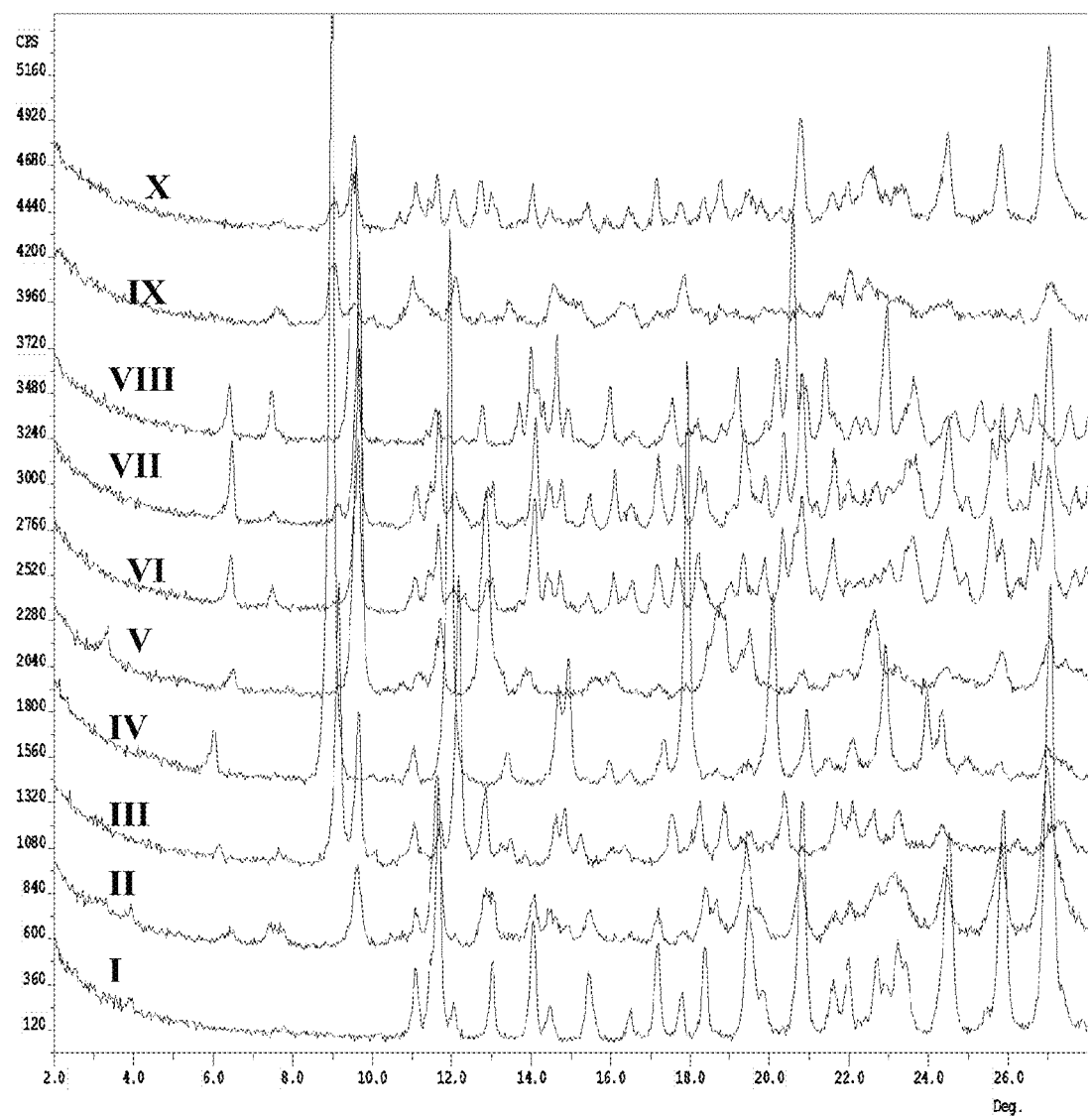
FIG. 3. Powder X-ray Diffraction patterns of the ten unique solids obtained from the polymorph screening study (See Example 5). Form I through Form X as designated in Tables 5 and 6 are presented.
Figure 4:
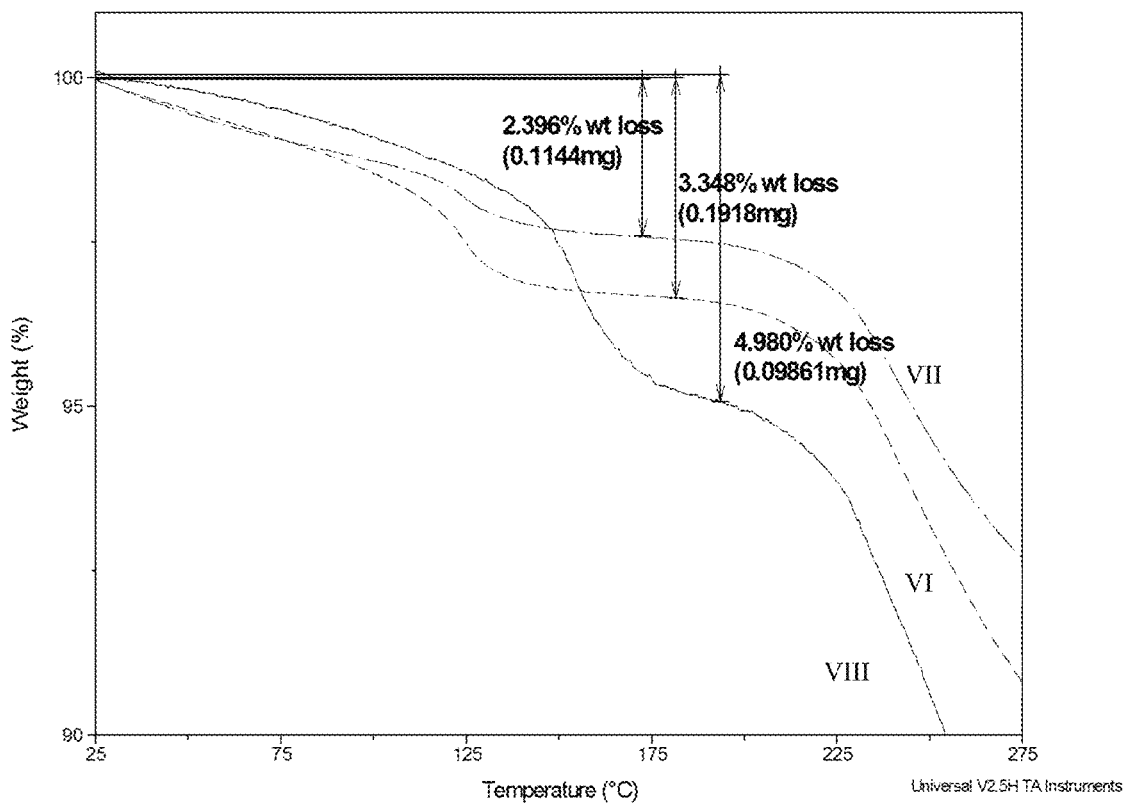
FIG. 4. TGA curves of solids from $CH_2Cl_2$ (Form VI, immediately after precipitation), Hexane (Form VII, after standing overnight), and acetonitrile (Form VIII, after standing 3 days).

The TGA curve showed abrupt weight loss at about 124° C. and 153° C. for the solids obtained from hexane and acetonitrile respectively, coupled by an endotherm at a similar temperature on DSC. Therefore, they also appeared to contain restrained solvent in crystal lattice. The stoichiometries of the retained solvents are about 0.6 for acetonitrile and about 0.14 for hexane. Needle-shaped crystals were grown from acetonitrile after standing for three days. The PXRD patterns of the acetonitrile-retaining solid were unique while the PXRD pattern of the hexane solvate is similar to the $CH_2Cl_2$-retaining solid identified earlier (FIG. 3). Both solvent-retaining solids (hexane and acetonitrile) lost weight on a TGA pan. Unique PXRD patterns of both solids were observed after the corresponding retained solvent had been removed by heating (Table 7, FIG. 3), indicating that removal of solvent molecules from the solids caused structural changes of the solvate crystals (therefore, the solvent molecules are in crystal lattice not just on crystal surfaces). However, the PXRD pattern of acetonitrile desolvate was low in signal intensity. DSC profile of the acetonitrile desolvate exhibited two additional heat events at 74° C. and 174° C., when compared with the DSC

TABLE 5

Physical characterization of solids isolated immediately after precipitation

| Name Assigned to PXRD pattern | Organic solvent | PXRD crystallinity | Microscopic observation | TGA wt % loss$^a$ | Thermal events by DSC (° C.)$^b$ | Color of the solid | Free flowing? (Y = yes; N = no) |
|---|---|---|---|---|---|---|---|
| Form I | Water + ACN | High | Irregular | 0.3 | 296 | Orange | Y |
| Form II | EtOH | Poor | Aggregate$^e$ | 2.5 | 81 $^c$, 226, 293 | Yellow | N (sticky) |
| Form I | MeOH | High | Irregular | 1.7 | 298 | Orange-red | Y |
| Form III | Acetone | Medium | Aggregate$^e$ | 2.5 | 88 $^c$, 155, 222, 228, 286 | Yellow | N (sticky) |
| Form IV | Acetonitrile (ACN) | High | Aggregate$^e$ | 2.9 | 97 $^c$, 142, 156, 172, 227, 230, 281 | Yellow | N (sticky) |
| Form V | THF | High | Aggregate$^e$ | 2.5 | 82 $^c$, 161, 175, 227, 292 | Yellow | N (sticky) |
| ND$^f$ | Ethyl acetate | Poor | Fine particles | 4.7 | 98 $^c$, 196, 222 | Light-orange | N (sticky) |
| ND$^f$ | Hexane | Poor | Aggregate$^e$ | | | Light-Orange | N (sticky) |
| Form VI $^g$ | $CH_2Cl_2$ | Medium | Plate + equant + fine | 3.3 | 123 $^d$, 164, 228, 296 | Orange-red | Y |
| ND$^f$ | IPA | Poor | Aggregate$^e$ | 1.9 | 76 $^c$, 222, 229, 296 | yellow | N (sticky) |

$^a$ Weight loss up to 160° C.
$^b$ For clarity, the temperatures listed in the table are peak temperatures only.
$^c$ Peak temperatures of a broad endothermal event from the starting temperature of a DSC run. These events are also reflected by gradual weight loss on TGA. This type of heat event is typical of loss of surface adsorbed solvent.
$^d$ Peak temperatures of a relatively sharp endothermal event on DSC. This event is also recorded by TGA as a sudden loss of weight at the corresponding peak temperature. This type of heat event is typical of desolvation of a solvate.
$^e$ The aggregates are constituted of very fine particles.
$^f$ ND means that no definite form can be assigned because of the low signal of the diffraction peaks of corresponding PXRD patterns obscured a detailed comparison with PXRD patterns of other forms.
$^g$ Form VI, is a solvent containing solid.

Example 6C

Precipitation After Standing up to Three Days in Solvent

These results are summarized in Table 6. After a standing time of up to three days in the solvent, a new non-fluffy orange-red solid phase appeared. The fluffy precipitates obtained from all organic solvents, except the precipitate from methanol, underwent transformation. Apparently, the solids precipitated immediately after precipitation were metastable in these cases in that they converted to a more stable solid form (Form I) over time. This conversion appeared to be completed in a couple of hours in most of the solvent systems. However, they were allowed to stand for a much longer period of time to ensure the completion of the process in order to avoid reaping a mixture of two solid forms.

profile of the acetonitrile solvate, while the desolvation event at 153° C. was absent. Cooling of the sample after desolvation may have changed the solid that undergoes an energetic change at 174° C.

When other organic solvents were used, the longer standing period of the precipitates yielded solids of the same PXRD pattern as that of Form I (Lot 35282-CS-51) although the morphology of the crystals was different (Table 6). The same PXRD pattern indicated that those solids have the same crystal lattice structure. The different morphology must be due to the solvent effects. It is apparent that Form I is the most stable solid phase among all non-solvated polymorphs reported herein. Other solvent-free solid forms were metastable and converted to Form I quickly when in contact with solvent. The solid from $CH_2Cl_2$ appeared to flow more easily than the solid from hexane. The TGA, morphology, and the flowability indicated that they are two different solids.

TABLE 6

Physical characterization of solids isolated after varying standing periods after precipitation

| Name Assigned to PXRD Pattern | Organic solvent (standing period) | PXRD crystallinity | Microscopic observation | wt % loss[a] | Thermal events by DSC (° C.)[b] | Color of the solid | Free flowing? (Y = yes; N = no) |
|---|---|---|---|---|---|---|---|
| Form I | Water + ACN | High | irregular | 0.3 | 296 | Orange | Y |
| Form I | Ethyl acetate (overnight) | High | Tablets | | | Orange-red | Y |
| Form VII [g] | Hexane (overnight) | Medium | plates | 2.4 | 124 [c], 228, 295 | Orange-red | N |
| Form I | IPA (overnight) | High | equant (25 um) + fine | 0.4 | 297 | Orange-red | Y |
| Form I | CH$_2$Cl$_2$ (overnight) | High | equant (25 um) + fine | 0.6 | 293 | Orange-red | Y |
| Form I | EtOH (3 days) | High | Aggregate[e] | | | Orange-red[d] | Y |
| Form I | Acetone (3 days) | High | plates | | | Orange-red[d] | Y |
| Form VIII [g] | Acetonitrile (3 days) | Medium | needles | 4.9 | 153 [c], 229, 231, 239, 291 | Orange-red[e] | N |
| Form I | THF (3 days) | High | Spear head | 0.3 | 295 | Light orange[f] | N |
| Form I | MeOH (overnight) | high | | | | Orange-red | Y |
| Form I | MEK (overnight) | high | rods | 0.6 | 297 | orange | N |
| Form I | dioxane (overnight) | high | plates | | 295 | orange | N |

[a]Weight loss up to 160° C. by TGA.
[b]For clarity, the temperatures listed in the table are peak temperatures only.
[c] Peak temperatures of a relatively sharp endothermal event on DSC. This event is also recorded by TGA as a sudden loss of weight at the corresponding peak temperature.
[d]Conversion was complete in 5 hrs (from yellow to orange-red).
[e]Conversion was not obvious in 5 hrs but was mostly completed in three days (yellow loose precipitate to orange-red well-formed needle-shaped crystals).
[f]Conversion was complete in 5 hrs. The color change was not obvious (from yellow to light orange).
[g] Form VII and VIII are solvent containing solids.

TABLE 7

Physical characterization of solids produced after desolvation.

| Name Assigned to PXRD pattern | Method of crystal generation | PXRD crystallinity | Thermal events by DSC (° C.) | Color of the solid |
|---|---|---|---|---|
| Form IX | Desolvation of ACN solvate | Poor | 74, 174, 229, 231, 239, 291 | orange |
| Form X | Desolvation of hexane solvate | medium | | orange |

Example 7

Inhibition of KIT Phosphorylation in Canine Mast Cell Tumors

Purpose.

The development of targeted therapies for cancer offers the opportunity to directly evaluate drug effects on the molecular target and correlate these effects with tumor biology and drug pharmacokinetics. This can be instrumental in oncology drug development because it establishes a pharmacodynamic/pharmacokinetic relationship and provides critical information in regarding the therapeutic impact of a targeted agent. The purpose of this study was to evaluate the effect of a single dose of the receptor tyrosine kinase inhibitor Compound I phosphate on the activity of its molecular target KIT in canine mast cell tumors (MCT), in canine patients with advanced MCTs using KIT phosphorylation as a marker of direct target inhibition. Also studied was phosphorylation of ERK1/2 (a mitogenactivated protein kinase (MAPK) downstream of KIT signaling), Compound I phosphate plasma concentration, and the mutational status of c-kit to determine how these parameters correlate with KIT phosphorylation status after Compound I phosphate treatment.

Study Drug.

Compound I phosphate was available in 20-mg scored tablets.

Study Design.

This study was a proof of target modulation study in dogs with recurrent or metastatic grade II/III MCTs. Patients received a single oral dose of Compound I phosphate at 3.25 mg/kg. Using a 6-mm punch biopsy instrument, samples were obtained from the tumor before Compound I phosphate administration and 8 hours (h) after treatment. When possible, multiple biopsies were taken. Each sample was flash frozen in liquid nitrogen and stored at −70° centigrade (C) before analysis. Blood samples for analysis of plasma levels of Compound I phosphate were obtained at the same time as tumor biopsies (see below).

Compound I Phosphate Plasma Levels.

Blood samples were drawn from the jugular vein and placed into a red-top serum collection vacuum glass tube. Specimens were kept at room temperature, allowed to clot, centrifuged at 1500 rpm at 4° C. for 10 minutes, transferred to cryovials, and plasma frozen at −70° C. pending analysis. Briefly, plasma samples (20 μl) or Compound I phosphate standards in canine plasma were mixed with methanol (200 μl) containing DL-propranolol hydrochloride (internal standard) in a 96-well polypropylene plate (Orochem Technology, Westmont, Ill.). The plate was mixed by vortex for 1 min, and the samples were centrifuged for 10 min at 4000 rpm. Ten microliters of the supernatant were injected onto the LC/MS/MS system, in which separation occurred on a BataBasic C-18 (5 µm, 100×4.6 mm) reverse-phase high-performance liquid chromatography column (Keystone Scientific, Foster City, Calif.). The amount of Compound I phosphate and the internal standard in each canine plasma sample were quantified based on standard curves generated using known amounts of compound ranging from 0.2 to 500 ng/ml.

c-kit Mutation Analysis.

For the majority of the samples, RNA was extracted using TRIzol (Invitrogen, Carlsbad, Calif.) according to the manufacturer's specifications. cDNA was then generated from the RNA using dNTPs, random primers, 5× First Strand Buffer, 0.1 M DTT, and Superscript Taq polymerase (all from Promega, Madison, Wis.). The cDNA was quantified for each sample. For the remaining samples, genomic DNA was prepared as described previously (Downing, S., Chien, M. B., Kass, P. H., Moore, P. F., and London, C. A. Prevalence and importance of internal tandem duplications in exons 11 and 12 of c-kit in mast cell tumors of dogs. Am. J. Vet. Res., 63: 1718-1723, 2002; which is incorporated by reference in its entirety). For both reactions, the PCR was run for 40 cycles consisting of 94° C. (1 min), 59° C. (1 min), and 72° C. (1 min), with a 5 min 72° C. extension at the end of the reaction. A c-kit cDNA generated from the canine C2 mast cell line and cDNA generated from normal canine cerebellum were used as controls.

The PCR products were separated by electrophoresis on a 4% agarose gel; the expected wild-type c-kit PCR product is 196 bp in size for PCR from cDNA and 190 bp in size for genomic DNA PCR. For those cases in which an ITD was not obvious (only a single band was present), the PCR products were gel purified using the Promega PCR Wizard Clean-Up kit (Promega) and sequenced using both P1 (forward) and P5 or P2 (reverse) primers at the core sequencing facility at the University of California—Davis, to rule out the presence of very small ITDs, deletions, or point mutations. Sequence alignment and comparison were performed using the DNA-SIS sequence analysis program.

Analysis of KIT and ERK Phosphorylation.

Tumor biopsies were frozen in liquid nitrogen and later pulverized using a liquid nitrogen-cooled cryomortar and pestle, then stored at −70° C. until used. For the analysis of KIT, pulverized tumors were homogenized, lysed, and immunoprecipitated from 1 mg of starting tumor lysate, as described previously (Abrams, T. J., Lee, L. B., Murray, L. J., Pryer, N. K., Cherrington, J. M. SU11248 inhibits KIT and platelet-derived growth factor receptor beta in preclinical models of human small cell lung cancer. Mol. Cancer Ther. 2: 471-478, 2003; which is incorporated by reference in its entirety) using an agarose-conjugated antibody to KIT (SC-1493AC; Santa Cruz Biotechnology, Santa Cruz, Calif.). When multiple biopsies were available, repeat immunoprecipitation/Western blot analysis was performed on separate biopsies. The amount of phosphorylated KIT in each sample was determined by Western blot using an antibody to phosphotyrosine 719 of murine KIT (3391; Cell Signaling Technology, Beverly, Mass.), which corresponds to tyrosine 721 of canine KIT and is an autophosphorylation site and, thus, a surrogate for KIT kinase activity. For the analysis of total KIT, the blots were stripped, reblocked, and reprobed with an antibody to KIT (A-4542; DAKO Corp., Carpinteria, Calif.). For analysis of p42/44 ERK, the same tumor lysates used for KIT analysis were probed by Western blot with an antibody to phospho-Thr 202/Tyr 204 ERK1/2 (9101B; Cell Signaling Technology) and then stripped and reprobed with an antibody to total ERK (9102; Cell Signaling Technology). Evaluable tumor biopsy pairs for both KIT and ERK1/2 were considered those for which detectable total protein was present in both biopsies of the pair. Target modulation was scored by eye by three observers blinded to the JM status and plasma concentration. Reduction of ≥50% in phospho-protein signal relative to total protein signal in the biopsy sample taken post-treatment compared with the pretreatment biopsy was scored as positive for target modulation, whereas a reduction of <50% was scored negative.

Results.

Fourteen dogs were enrolled in this clinical study with the primary objective to determine whether a reduction in KIT tyrosine phosphorylation occurred after oral administration of a single dose of Compound I phosphate. KIT tyrosine phosphorylation was assessed using a phospho-specific antibody directed against an autophosphorylation site in KIT, serving as a surrogate for KIT kinase activity. In addition, c-kit JM mutational status (ITD+ or ITD−) was determined from the baseline tumor biopsy, and plasma concentrations of Compound I phosphate were measured 8 hours after dosing to correlate these parameters with inhibition of KIT phosphorylation. Eleven of the 14 dogs were evaluable for KIT target modulation. The three dogs deemed not evaluable had undetectable or greatly reduced total KIT protein in one or both biopsies and so could not be scored for target modulation. The data for all dogs enrolled in the study are summarized in Table 8.

TABLE 8

Summary data for all patients enrolled

| Patient number | Tumor grade | c-kit ITD mutation present | Plasma Compound I phosphate postdose (ng/mL) | P-KIT reduction postdose[a] | P-ERK1/2 reduction postdose |
|---|---|---|---|---|---|
| 1 | III | Yes | 81.0 | Yes | No |
| 2 | III | Yes | 33.2 | Yes | No |
| 3 | II | Yes | 83.5 | NE | Yes |
| 4 | III | Yes | 98.0 | Yes | Yes |
| 5 | III | Yes | 116.0 | Yes | Yes |
| 6 | III | No | 121.0 | Yes | Yes |
| 7 | III | No | 186.0 | NE | NE |
| 8 | III | No | 0.3 | Yes | No |
| 9 | II | No | 103.0 | NE | NE |
| 10 | II | No | 111.0 | No | Yes |
| 11 | II | No | 158.0 | No | Yes |
| 12 | II | No | 65.3 | Yes | Yes |
| 13 | II | No | 95.4 | No | No |
| 14 | III | No | 119.0 | Yes | NE |

[a]NE, nonevaluable, P-KIT, Phospho-Tyr721 KIT, P-ERK1/2, Phospho-Thr202/Tyr204 ERK1/2

Figure 5:
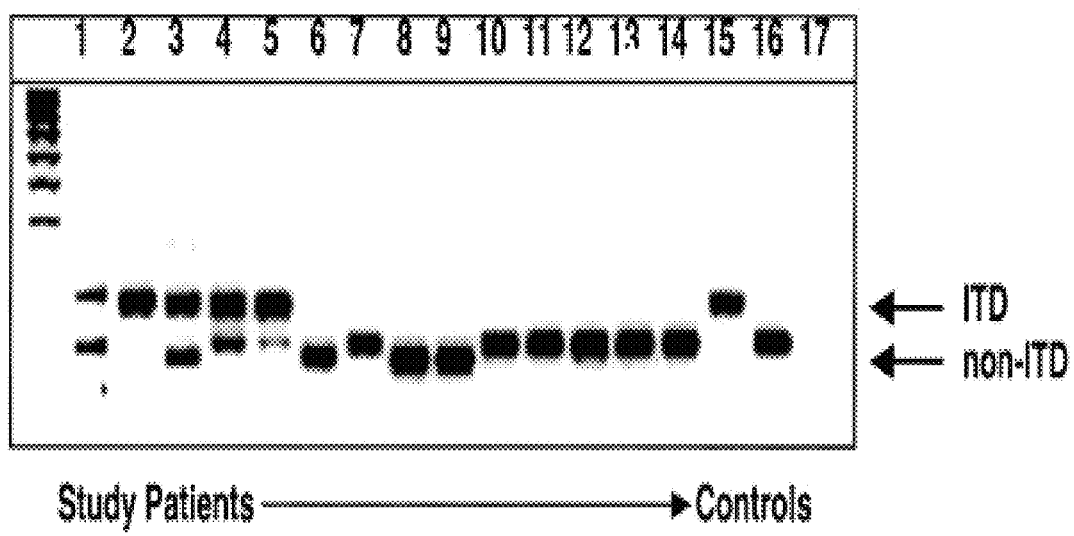
FIG. 5. Results of agarose gel electrophoresis of PCR products from MCTs evaluated in FIG. 6. Reductions in MCT phosphorylated KIT and phosphorylated extracellular signal-regulated kinase (ERK)1/2 after a single dose of Compound I phosphate Example 7. Lanes 1-5 correspond to patients 1-5 in Table 8; Lanes 6-14 correspond to patients 6-14 in Table 8. Controls consisted of PCR products generated from the C2 canine mast cell line containing a 48-bp ITD (Lane 15) and from normal canine cerebellum (wild type; Lane 16).

Of the 14 dogs analyzed, 5 (36%) had an ITD by PCR analysis (FIG. 5, Lanes 1-5); all five tumors had evidence of an ITD. Interestingly, patient 2 had apparently lost the wild-type c-kit allele. The PCR products from the remaining nine dogs that did not have evidence of an ITD (FIG. 5, Lanes 6-14) were directly sequenced, and none demonstrated any type of mutation (insertion, deletion, or point mutation). For Lanes 3, 6, 8, and 9, genomic DNA was used for the PCR reaction, resulting in a slightly smaller (190 bp) wild-type product.

Figure 6:
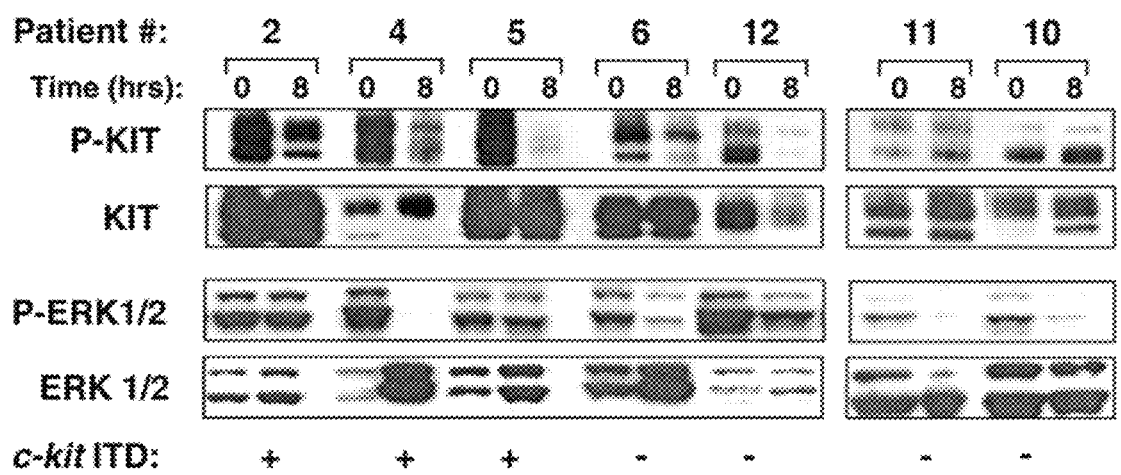

The level of total and phosphorylated KIT expressed in the MCTs at baseline varied between animals. Higher KIT expression correlated with higher tumor grade. Four of eight grade III tumors had high KIT expression, compared to one of six grade II tumors (FIG. 6). For example, the total KIT expression in the tumor from patient 2 (grade III) was markedly higher than that in the tumor from patient 11 (grade II). Dogs with grade III tumors also had a higher incidence of high levels of phosphorylated KIT at baseline than those with grade II tumors, consistent with the increased frequency of c-kit ITD mutations in advanced tumors and consequently elevated levels of ligand-independent phosphorylated KIT. Five of the evaluable seven dogs with grade III tumors had high levels of phosphorylated KIT at baseline; four of these were positive for the presence of an ITD in c-kit. Only 1 grade II tumor had significant phosphorylated KIT; this animal also expressed ITD-mutated c-kit.

Eight of the 11 evaluable dogs scored positive for target modulation using the criterion of a ≥50% reduction in phosphorylated KIT relative to total KIT in the biopsy sample taken after Compound I phosphate treatment when compared with the pretreatment sample. Examples of phosphorylated KIT and total KIT in immunoprecipitates of tumor biopsies taken before and after treatment with Compound I phosphate are shown in FIG. 6. Five tumors (FIG. 6, left) were scored as positive for target modulation, whereas two tumors (FIG. 6, right) were scored as negative. Biopsy pairs that were scored as negative for inhibition of KIT phosphorylation after Compound I phosphate treatment all had markedly less phosphorylated KIT at baseline than those that scored positive (FIG. 6).

To evaluate effects of Compound I phosphate inhibition on downstream signaling pathways regulated by KIT phosphorylation, levels of the phosphorylated MAPK ERK1/2 were evaluated by Western blot analysis of the same biopsy pairs used for KIT analysis. Eleven of 14 tumors were evaluable for phospho-ERK1/2 target modulation (two of these were also nonevaluable for KIT target modulation). Of the 11 evaluable, 7 showed a reduction in the ratio of phospho-ERK1/2 to total ERK1/2 in tumors sampled after the administration of Compound I phosphate, compared with baseline tumor samples (see FIG. 6). ERK target modulation was more frequently detected in MCTs with relatively high baseline ERK expression and phosphorylation than in those with low ERK.

Based on preclinical work in rodent models, the therapeutic range of Compound I for target inhibition was considered to be 50-100 ng/ml for 12 h of a 24-h dosing period. The plasma concentration of Compound I phosphate at 8 h (approximately Cmax) after a single dose at 3.25 mg/kg ranged from 33.2 to 186 ng/ml, with an average of 105±9 ng/mL (Table 8). In one animal, the plasma concentration of Compound I phosphate was outside the range of the other samples (0.3 ng/ml). Twelve of 14 dogs had plasma levels considered to be in the therapeutic range established in a Phase I clinical study of Compound I. (London, C. A., Hannah, A. L., Zadovoskaya, R., Chien M. B., Kollias-Baker, C., Rosenberg, M., Downing, S., Post, G., Boucher, J., Shenoy, N., Mendel, D. B., and Cherrington, J. M. Phase I dose-escalating study of SU11654, a small molecule receptor tyrosine kinase inhibitor, in dogs with spontaneous malignancies. Clin. Cancer Res., 2755-2768, 2003) The average plasma concentration for dogs with evidence of KIT target modulation (79.2±41 ng/ml) and those that did not score for KIT target modulation 137±36 ng/ml) was not significantly different (P=0.08).

Discussion.

This correlative study was designed to investigate target modulation in a comparable clinical population by studying the effects of a single clinically efficacious dose of Compound I phosphate on the phosphorylation of KIT in canine MCTs and the subsequent impact on signaling through MAPKs. The plasma concentrations of Compound I phosphate achieved in this study were measured near the expected Cmax, based on preclinical pharmacokinetic studies and were consistent with drug levels measured in the Phase I clinical study investigating the efficacious dose and regimen of Compound I (Table 8).

Eight of 11 (73%) evaluable MCT biopsy pairs had detectable inhibition of KIT activation as measured by a reduction in phosphorylated KIT after a single oral dose of Compound I phosphate. The three patients that did not show detectable KIT target modulation after treatment had MCTs that expressed low levels of KIT and phospho-KIT at baseline. The lack of significant target modulation in these patients may be attributable to technical limits in the detection method; the sensitivity of the phospho-specific antibody for phosphorylated KIT relative to nonphosphorylated KIT may be insufficient in samples with low baseline KIT expression Inhibition of KIT activity correlated more closely with baseline KIT phosphorylation than with c-kit ITD genotype. Based on cellular assays, it would be predicted that both wild-type and ITD mutant KIT would be inhibited by Compound I phosphate in vivo, because Compound I in vitro blocked the phosphorylation of wild-type and ITD mutant KIT with comparable potency.

Compound I phosphate also affected a signaling pathway downstream of KIT. Mutations in c-kit in GIST and hematopoietic malignancies have been reported to activate different signaling pathways from each other and from wild-type KIT. In canine MCTs, all but one tumor sample had detectable phosphorylated ERK1/2 at baseline. In 7 of 11 evaluable tumor biopsy pairs, ERK1/2 was inhibited, as measured by a reduction in phosphorylated ERK1/2 after treatment. Not all of the tumors scoring positive for ERK1/2 inhibition were also positive for inhibition of KIT phosphorylation. ERK1/2 target modulation did not correlate with tumor grade or the presence or absence of c-kit ITD mutation. As for KIT target modulation, ERK1/2 target modulation was detected more frequently in tumors that expressed high levels of ERK1/2 and phosphorylated ERK1/2 at baseline.

The detection of inhibition of a molecular target of Compound I phosphate after treatment of MCTs serves as proof of target modulation for Compound I phosphate in this setting. The clinical relevance of this finding is supported by the correlation between inhibition of the molecular target and plasma drug concentrations in the therapeutic range, and the previously reported clinical objective responses to Compound I in canine patients with MCTs expressing activating mutations in the target gene, providing proof of concept for Compound I phosphate in this population of patients. Because dogs with other malignancies (including mammary carcinoma, soft tissue sarcoma, and multiple myeloma) also experienced durable objective responses on treatment with Compound I, KIT inhibition at this plasma concentration may be reasonably extrapolated to successful inhibition of the other closely related receptor tyrosine kinase targets of Compound I expressed by these tumors, based on in vitro and in vivo potency of Compound I, providing a molecular rationale for objective responses in these tumors. For example, canine mammary tumors express VEGFR, which is inhibited by indolinone tyrosine kinase inhibitors at comparable concentrations to KIT in cellular in vitro assays. (Liao, A. T., Chien, M. B., Shenoy, N., Mendel, D. B., McMahon, G., Cherrington, J. M., and London, C. A Inhibition of constitutively active forms of mutant kit by multitargeted indolinone tyrosine kinase inhibitors. Blood, 100: 585-593, 2002) Compound I phosphate inhibition of both wild-type and ITD mutant c-kit in MCTs can, thus, serve as a surrogate for inhibition of the related RTK targets of Compound I phosphate, VEGFR, and PDGFR, which are aberrantly expressed and/or regulated by many different tumor types. Finally, molecular target inhibition, coupled with clinical objective responses in canine tumors, directs the development of

Example 8

Multicenter, Placebo-Controlled, Double Blind, Randomized Study of Oral Compound I Phosphate in the Treatment of Dogs with Recurrent Mast Cell Tumors Purpose.

The effectiveness of Compound I phosphate oral tablets for the treatment of mast cell tumors in client-owned animals that had recurrent measurable disease after surgery was evaluated in a masked, negative controlled study. The study evaluated every-other-day dosing of Compound I phosphate at 3.25 mg free base equivalents (FBE)/kg body weight on disease response using modified (RECIST) criteria of response. The presence or absence of c-kit mutation in mast cell tumors was evaluated as a covariate in this study. For decision-making purposes, the duration of the study was 6 weeks.

One-hundred-fifty-three (153) dogs were randomized in a ratio of 4:3 into one of two treatment groups: T01 (Placebo in which n=65) and T02 (Compound I phosphate in which n=88). Ten veterinary oncology practices in the United States were selected and enrolled cases. For enrollment, dogs had to have recurrent mast cell tumor (at least one target lesion had to have a minimum longest diameter of 20 mm)±regional lymph node involvement. A maximum of three target lesions (measurable mast cell tumors) and all non-target lesions (all remaining lesions, measurable or un-measurable) were identified at baseline by two evaluators. Efficacy was based on the objective response (complete response or partial response) at the week 6 visit where the mean of the two evaluators sum of the longest diameter of target lesions (Mean Sum LD) was compared to the Baseline Mean Sum LD for calculation of percent reduction or increase. Assessment of non-target lesions was subjective. A complete response (CR) was defined as the disappearance of all target and non-target lesions and the appearance of no new lesions; a partial response (PR) was defined as at least a 30% decrease in the Mean Sum LD of target lesions compared to the Baseline Mean Sum LD and non-progression of non-target lesions and appearance of no new lesions. Tissue samples from the tumor and distant normal skin were collected prior to randomization and submitted for the assessment of c-kit mutation status.

Eighty-six (86) T02 and 65 T01 animals were included in the efficacy analysis. The data analysis indicated a statistically significant improvement in the primary endpoint (objective response) for Compound I phosphate (T02) compared to placebo (T01). The T02 animals had a significantly greater objective response rate (38.3%; 33/86) compared to T01 animals (7.9%; 5/63) ($p<0.001$). Nearly twice as many T01 animals (66.7%; 42/63) experienced progressive disease compared to T02 animals (33.7%; 29/86). Dogs in the T02 group that were positive for the c-kit mutation were almost twice as likely to have an objective response compared to those that were negative for the c-kit mutation (60%, 12/20 vs. 32.8%, 21/64, respectively).

In conclusion, this study demonstrated the effectiveness of Compound I phosphate oral tablets for the treatment of recurrent mast cell tumors in client-owned dogs.

Numerous modifications and variations in the invention as set forth in the above illustrative examples are expected to occur to those skilled in the art. Consequently, only such limitations as appear in the following claims should be placed on the invention.

What is claimed is:

1. A polymorph of the citrate salt of 5-[5-fluoro-2-oxo-1,2-dihydro-indol-(3Z)-ylidenemethyl]-2,4-dimethyl-1H-pyrrole-3-carboxylic acid (2-pyrrolidin-1-yl-ethyl)-amide, wherein said polymorph has a powder X-ray diffraction spectrum comprising peaks expressed in degrees (±0.1 degree) of two theta angle of 9.1, 9.4, 14.2, 25.4, and 26.8 obtained using CuK$\alpha_1$ emission (wavelength=1.5406 Angstroms) and wherein said polymorph has a melting point of about 178 to about 183° C.

2. A pharmaceutical composition comprising the polymorph of claim 1, and a pharmaceutically acceptable carrier or excipient.

3. A method for the modulation of the catalytic activity of protein kinases, comprising contacting said protein kinase with the polymorph of claim 1.

4. A method of claim 3, wherein the protein kinase is selected from the group consisting of receptor tyrosine kinases, non-receptor protein tyrosine kinases, and serine/threonine protein kinases.

* * * * *